US010799380B2

(12) United States Patent
Kalloo et al.

(10) Patent No.: US 10,799,380 B2
(45) Date of Patent: Oct. 13, 2020

(54) GASTRIC DEVICE AND METHOD OF USE THEREOF

(71) Applicant: THE JOHNS HOPKINS UNIVERSITY, Baltimore, MD (US)

(72) Inventors: Anthony N. Kalloo, Baltimore, MD (US); Mouen A. Khashab, Towson, MD (US); Darrin Kent, Murrieta, CA (US); Peter D'Aquanni, Murrieta, CA (US); Brett Hampton, Murrieta, CA (US)

(73) Assignee: The Johns Hopkins University, Baltimore, MD (US)

( * ) Notice: Subject to any disclaimer, the term of this patent is extended or adjusted under 35 U.S.C. 154(b) by 353 days.

(21) Appl. No.: 15/242,377

(22) Filed: Aug. 19, 2016

(65) Prior Publication Data

US 2017/0049598 A1    Feb. 23, 2017

Related U.S. Application Data

(60) Provisional application No. 62/207,587, filed on Aug. 20, 2015.

(51) Int. Cl.
*A61F 5/00* (2006.01)

(52) U.S. Cl.
CPC ............ *A61F 5/0036* (2013.01); *A61F 5/003* (2013.01); *A61F 5/0089* (2013.01)

(58) Field of Classification Search
CPC ...... A61F 5/0013; A61F 5/003; A61F 5/0036; A61F 5/0089; A61F 5/0003; A61F 5/0033
See application file for complete search history.

(56) References Cited

U.S. PATENT DOCUMENTS

| | | | |
|---|---|---|---|
| 4,416,267 A | | 11/1983 | Garren et al. |
| 4,598,699 A | * | 7/1986 | Garren ................. A61B 1/2736 604/909 |
| 4,739,758 A | | 4/1988 | Lai et al. |
| 5,603,950 A | | 2/1997 | Ratjen et al. |
| 5,868,141 A | | 2/1999 | Alias |
| 6,981,981 B2 | | 1/2006 | Reiley et al. |
| 8,075,582 B2 | | 12/2011 | Lointier et al. |
| 8,287,562 B2 | | 10/2012 | Kasic, II |
| 8,722,066 B2 | | 5/2014 | Costa |
| 2003/0049325 A1 | | 3/2003 | Suwelack et al. |
| 2003/0072804 A1 | * | 4/2003 | Hird ....................... A61K 9/122 424/486 |
| 2003/0091610 A1 | | 5/2003 | Hird et al. |
| 2005/0033331 A1 | | 2/2005 | Burnett et al. |
| 2006/0058829 A1 | | 3/2006 | Sampson et al. |

(Continued)

OTHER PUBLICATIONS

International Search Report dated Dec. 28, 2016, regarding PCT/US2016/047896.

*Primary Examiner* — Kathleen S Holwerda
(74) *Attorney, Agent, or Firm* — DLA Piper LLP (US)

(57) ABSTRACT

The present invention provides a low-risk, unobtrusive and noninvasive method and device for treatment of obesity and eating disorders. In embodiments, the device is a gastric device suitable for placement in a stomach of a subject. The device may be composed of a sponge material which absorbs fluid upon implantation and expands in volume, thereby functioning as a space occupying device in the stomach to cause early satiety.

34 Claims, 20 Drawing Sheets

(56) References Cited

U.S. PATENT DOCUMENTS

| | | |
|---|---|---|
| 2006/0276802 A1* | 12/2006 | Vresilovic ............. A61F 2/4611 606/102 |
| 2007/0100367 A1* | 5/2007 | Quijano ................. A61F 5/003 606/192 |
| 2007/0156248 A1 | 7/2007 | Marco et al. |
| 2008/0109027 A1* | 5/2008 | Chen ....................... A61F 5/003 606/191 |
| 2008/0234718 A1 | 9/2008 | Paganon et al. |
| 2008/0269555 A1 | 10/2008 | Paganon et al. |
| 2009/0082644 A1 | 3/2009 | Li |
| 2009/0192535 A1 | 7/2009 | Kasic, II |
| 2009/0259246 A1* | 10/2009 | Eskaros ................. A61F 5/003 606/192 |
| 2010/0100115 A1* | 4/2010 | Soetermans .......... A61F 5/0036 606/192 |
| 2010/0291266 A1 | 11/2010 | Czinki |
| 2011/0066175 A1 | 3/2011 | Gross |
| 2011/0295299 A1* | 12/2011 | Braithwaite ............ A61F 5/003 606/191 |
| 2012/0095495 A1* | 4/2012 | Babkes ................. A61F 5/0033 606/192 |
| 2012/0245553 A1 | 9/2012 | Raven et al. |
| 2012/0296365 A1 | 11/2012 | Nguyen |
| 2013/0231692 A1 | 9/2013 | Kalloo et al. |
| 2014/0243770 A1 | 8/2014 | Stewart et al. |
| 2014/0276330 A1 | 9/2014 | Costa |

\* cited by examiner

GASTRIC DEVICE AND METHOD OF USE THEREOF

RELATED APPLICATION DATA

This application claims the benefit of priority under 35 U.S.C. § 119(e) of U.S. Provisional Patent Application Ser. No. 62/207,587, filed Aug. 20, 2015, the entire contents of which is incorporated herein by reference in its entirety.

BACKGROUND OF THE INVENTION

Field of the Invention

The invention relates generally to treatment of obesity and eating disorders and more specifically to a gastric device for treatment of such disorders.

Background Information

Obesity is a complex metabolic disease that carries a severe toll of comorbid illness. Over the past few decades, obesity has evolved into a global epidemic, and it is now more prevalent than malnutrition from hunger. Obese patients are deemed to be surgery-eligible only if they were obesity class I (body mass index [BMI]>40 kg/m–) or obesity class II (BMI 35-39.9 kg/m$^2$) with significant associated comorbid illness. Although it is clear that increasing BMI is associated with a higher burden of comorbid illness, stringent application of these well-rounded BMI categories in determining which patients are eligible for treatment leaves many without effective therapeutic options. For patients who do not meet these criteria, lifestyle modification and medications have been recommended; however, these have been of limited effectiveness and durability, with high rates of attrition. Alternatively, surgical intervention is effective and provides durable results for many patients but with a substantially higher risk profile. The reduced risk profile and unique characteristics of endoscopic obesity procedures may allow the introduction of new categories of procedures with different points of intervention. Thus, a need exists for a low risk and effective strategy to assist obese patients with weight reduction.

SUMMARY OF THE INVENTION

The present invention provides a low-risk, unobtrusive and minimally invasive method and system for treatment of obesity and eating disorders.

Accordingly, in one aspect, the present invention provides a gastric device. The gastric device is suitable for placement in a stomach of a subject to provide the subject with a sensation or perception of satiety. In embodiments, the device is a sponge which includes a core region composed of an open cell foam material that is substantially acid resistant and non-degradable, and which expands in volume upon absorption of fluid; and optionally an outer casing disposed about the core region, the outer casing being composed of a material that is substantially acid resistant and non-degradable, such as silicon or PEBAX. The outer casing includes one or more openings operable to allow fluid flow across the casing to and from the core region. In embodiments, the core region is composed of a material that is degradable after a certain time period has elapsed such that the device may be passed through the intestinal tract.

In another aspect, the present invention provides a method of treating obesity. The method includes introducing a gastric device of the present invention into the stomach of a subject, thereby treating obesity. In one embodiment, the sponge is introduced in a compressed configuration into the stomach, preferably by endoscopic delivery. Upon contact with fluid, the sponge expands in volume to assist in creating a feeling of satiety in the subject. In some embodiments, the sponge is introduced in a compressed configuration into the stomach via a lumen of a delivery device, such as an endoscope, and may be removed from the stomach by attachment to a retrieval device inserted through the delivery device and compression of the sponge as it is retracted by the retrieval device into the endoscope. In some embodiments, the gastric device is composed of non-expanding material having a predetermined deployed configuration which fills the stomach cavity. The device length is varied depending on the proportion of the stomach cavity to be filled.

In yet another aspect, the present invention provides a device operable to couple or grasp an object, such as a medical implant or the gastric device of the disclosure. The device includes an elongated shaft extending from a proximal end to a distal end along a longitudinal axis, the shaft having a lumen extending along the longitudinal axis, wherein the distal end comprises a coupling structure operable to couple to, or grasp an object, such as a gastric device. An actuator is disposed proximally on the shaft which is operable by a physician's hand to actuate the capturing structure. The actuator may be included in a handle or grip which may be removable. In embodiments, the device shaft is flexible or articulating. For example, the shaft may be composed of a semi-rigid material and/or be steerable. In one embodiment, the handle is operable to transition the distal coupling element from a first configuration to a second configuration to reversibly release or couple/grasp an object. In various embodiments, the device may be utilized to retrieve a gastric device from the stomach of a subject. Further, the shaft may include one or more markers for determining the location of the device and/or implant.

In yet another aspect, the invention provides a system which includes one or more gastric devices of the invention along with a delivery device having a lumen for delivery or retrieval of the sponge from the stomach. The system may further includes a device of the invention having a coupling structure and optionally a capture tube, both of which may be used for delivery and/or retrieval of an object, such as a gastric device.

DETAILED DESCRIPTION OF THE INVENTION

The present invention provides a minimally invasive and effective method for treatment of obesity and eating disorders via a gastric device and system. The method and devices have many advantages over current methodologies, such as minimal invasiveness, low cost, availability of biocompatible sponge materials, repeatability of the implantation and removal procedure, and use as a bridge to surgery (for morbidly obese patients who are not fit for surgery due to their extreme overweight). The procedure to implant the device in the stomach can be entirely performed in a minimally invasive procedure by endoscopic introduction into the stomach. Additionally, the device can be easily removed from the stomach when needed.

Before the present device and method are described, it is to be understood that this invention is not limited to the particular configuration and method described. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Figure 18:
FIG. 18 is a capture tube 500 for use with the gastric device in one embodiment of the invention. The tube may be used for delivery and retrieval of an implant. The tube includes a manicured distal tip 510 and proximal handle 520 which maybe coupled to an overtube (not shown). The tube may be semi-flexible (LPDE). The manicured tip improves deliverability through an overtube and the tip may include an inner diameter chamfer to facilitate implant retrieval.
Figure 19:
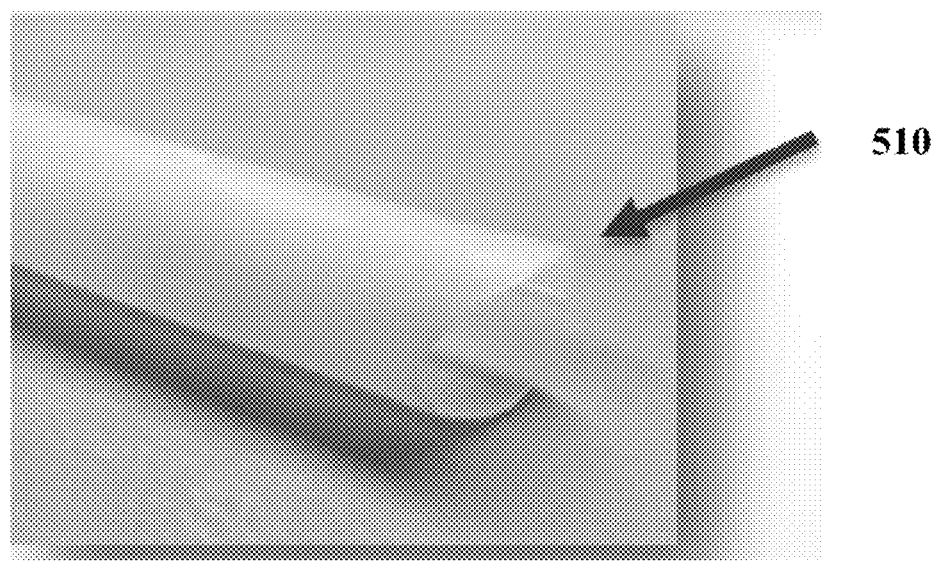
FIG. 19 is an expanded view of the manicured tip 510 of the tube of FIG. 18.
Figure 20:
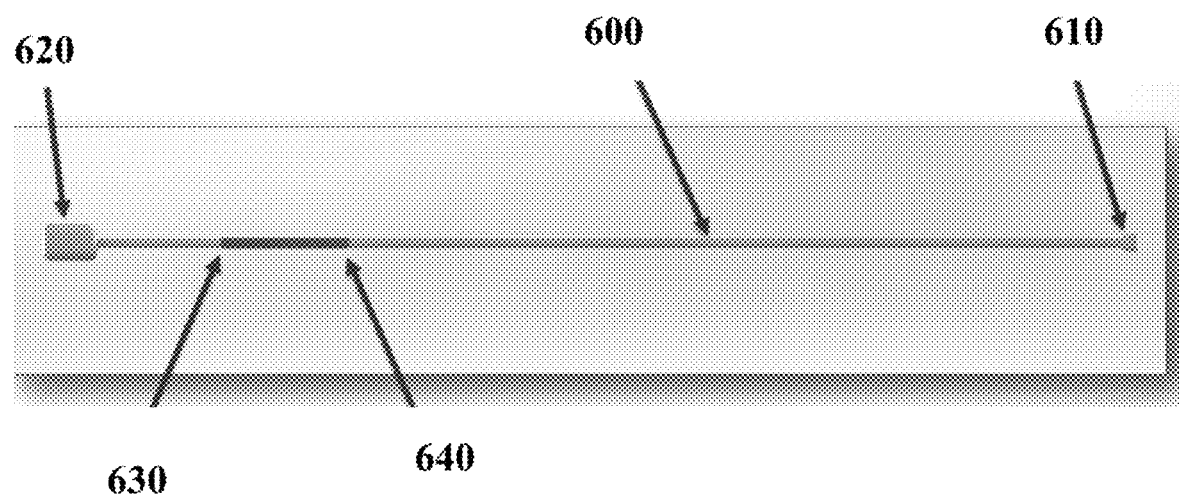
FIG. 20 is a schematic view of a pusher device 600 suitable for delivery of an implant. The pusher device 600 has a distally disposed pusher structure 610 for advancing an implant through a delivery lumen during delivery of an implant along with a proximal handle 620. Proximal 630 and distal 640 markers are disposed on the shaft for determining implant positioning.

In one aspect, the present invention provides a gastric device and a system which includes a gastric device, such as a sponge device, and optionally, a delivery and retrieval device suitable for luminal delivery of the sponge to the gastric cavity, such as an endoscope, catheter, or overtube. The system may further include a retrieval device operable to couple to a deployed sponge. By way of illustration, such a device includes endoscopic retrieval devices, including, for example, hook, net, basket or snare type devices, forceps, graspers, suction devices, as well as magnetic retrieval devices. As such, in various embodiments, the gastric device may include features to facilitate retrieval, such as for example, capture elements, loops, hook-loop type fasteners (i.e., Velcro®), magnets, and the like. In one embodiment, the retrieval device is described herein, for example, as shown in FIGS. 21-25 which is configured to engage a loop on the gastric device. The system may further include a pusher device (FIG. 20) and/or a capture tube (FIGS. 18-19) as described herein to facility delivery and retrieval of the gastric device.

The term scope device or endoscope, as used herein, should be construed as including all types of invasive instruments, flexible, articulating or rigid, having scope features.

As used herein, the term "gastric sponge", is intended to refer to a device that is formed to a size suitable for deployment in the stomach of a subject and, following deployment, expands to a size greater than the administration size upon contact with fluid. In this respect, "deployable" means that the device is capable of transitioning from a compressed state to an expanded state upon deployment.

The term "expandable", as used herein, means the ability of the device to expand upon hydration of the device material. As discussed in detail herein, the expandable gastric device of the invention exhibits the ability to absorb, as well as release fluid resulting in an increase and decrease in volume of the device respectively. Release of fluid and consequent reduction in volume of the device may result from external pressure or "squeezing" of the device during removal of the device or by pressure resulting from contraction of the stomach. Dynamic expansion and contraction of the sponge while present in the gastric space is especially advantageous, as the gastric adaption will not be able to occur over time; i.e., when the stomach expands to accommodate both a foreign object (e.g., a gastric balloon) and other solids (i.e., food).

Figure 1:
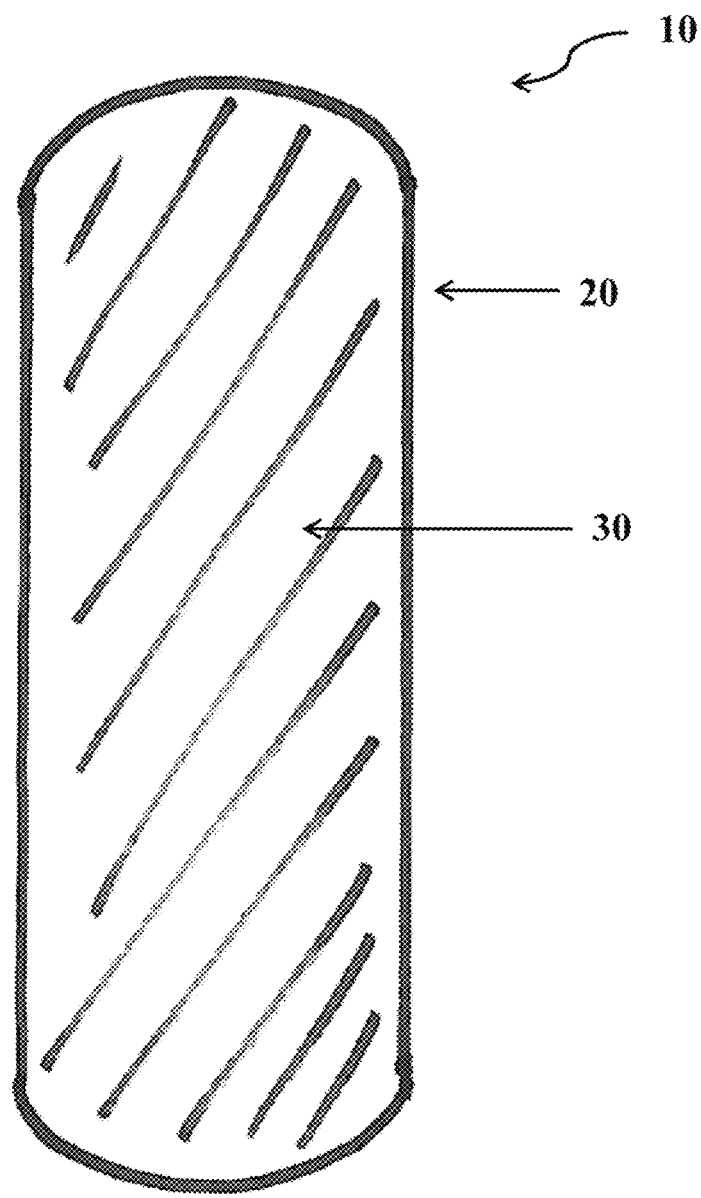
FIG. 1 is a cross-sectional view of a sponge device in one embodiment of the invention in an expanded state.

The system of the invention includes a gastric sponge device suitable for placement in a stomach of a subject. As depicted in FIG. 1, the device 10 includes a core region 20 and an outer casing 30 surrounding the core region. Both the core region 20 and surfaces of outer casing 30 are porous to allow fluid transfer into an out of the core region 20.

Figure 2:
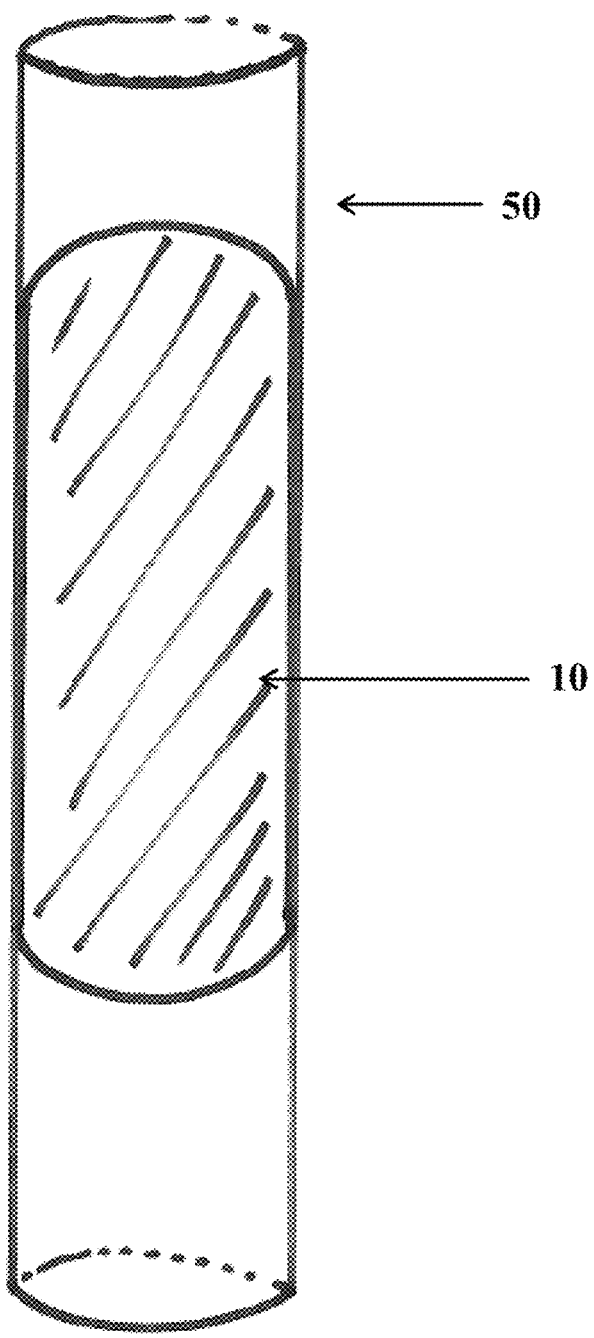
FIG. 2 is a schematic view of a sponge device in one embodiment of the invention in a compressed state with the lumen of a delivery device.

As shown in FIG. 2, prior to delivery, the sponge device may be compressed and have a generally cylindrical shape, for example the device generally conforms to the circular lumen of a delivery device. To facilitate delivery, the device 10 is compressed within the lumen of a delivery device 50 and advanced into a gastric space and subsequently deployed within the gastric space by advancing the device out of the lumen.

Figure 3:
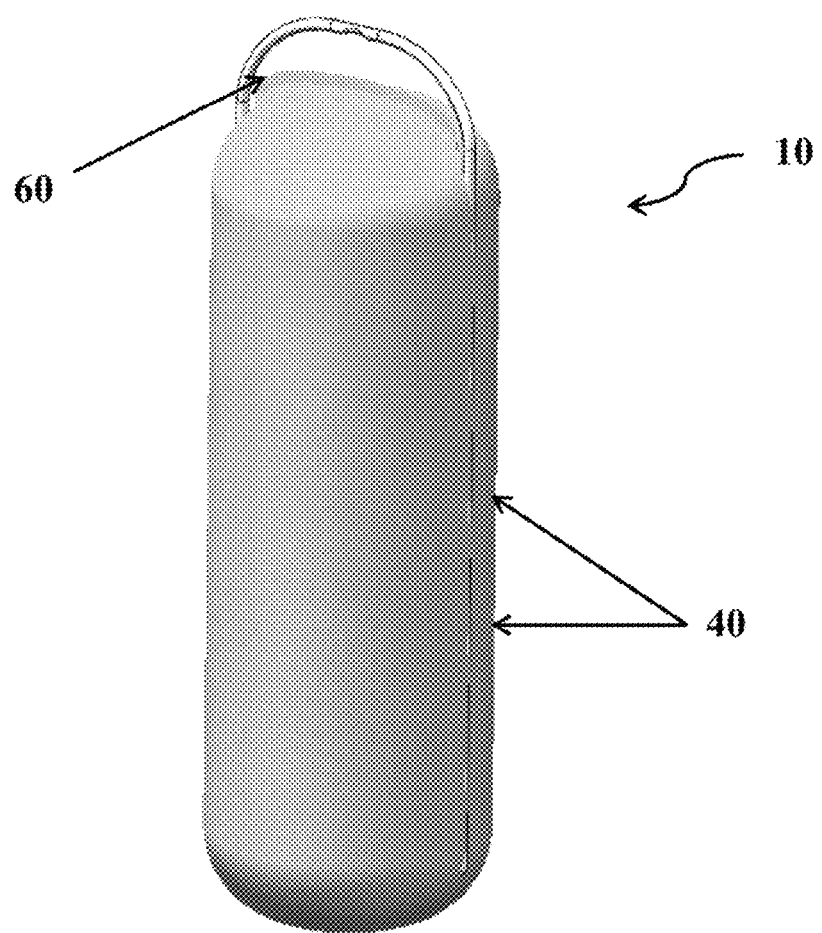
FIG. 3 is a schematic view of a sponge device in one embodiment of the invention in an expanded state.
Figure 5A:
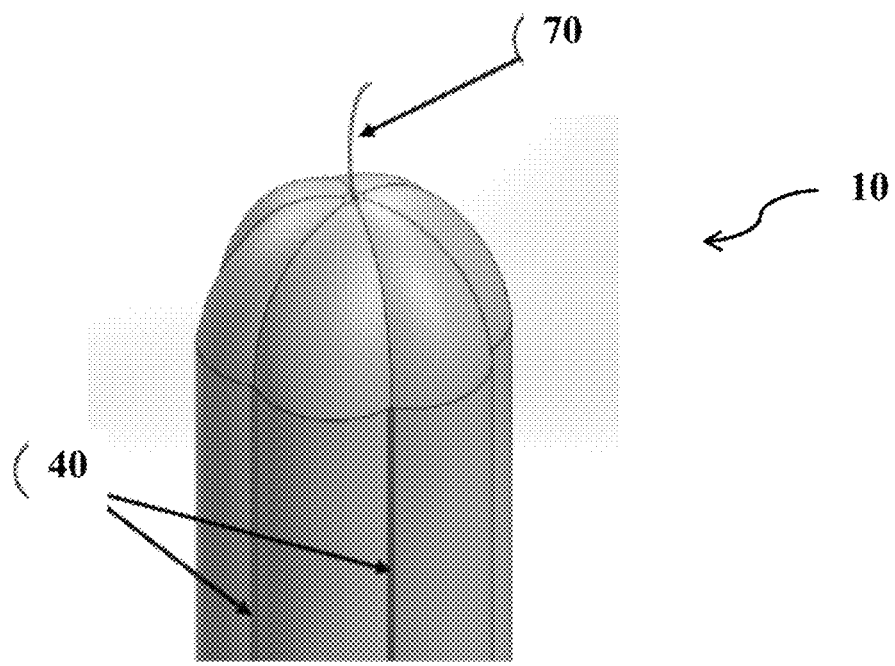
FIG. 5A is a partial side view of a sponge device in one embodiment of the invention.
Figure 5B:
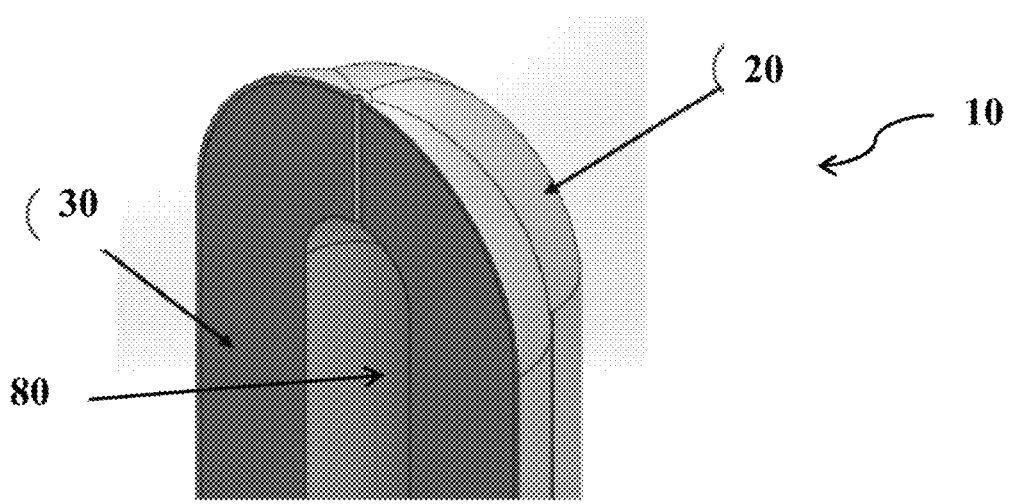
FIG. 5B is a cross-sectional view of the sponge device of FIG. 5A.

As illustrated in FIGS. 3 and 5A-5B, the outer casing may include one or more slits 40 to allow fluid passage to and from the core region thereby allowing the device to expand and contract in volume. Alternatively, or in addition to the slits, the casing 20 may be porous and include a plurality of microporous holes as discussed further herein. Once delivered, the device expands to a deployed state thereby adsorbing fluid from the gastric space. In some embodiments, the device has a generally cylindrical shape in the deployed state.

As discussed herein, the device can be compressed for insertion into or alongside an endoscope and deployable through the central lumen of a catheter and from the tip of the scope when placed at a target site, such as through the pyloric valve into the stomach. Deployment allows it to expand to assist in retention of the device in the stomach by preventing its passage through the pyloric valve.

The method and device of the present invention are useful for weight loss and treatment of obesity. Generally, the gastric sponge may be configured as a through-the-scope tool or in the form of a delivery cartridge that is delivered alongside the scope, and the methods for implantation and extraction of the device are performed to completion endoscopically. The sponge device absorbs fluid upon implantation and expands in volume, thereby functioning as a space occupying device in the stomach to cause early satiety.

As such, in another aspect, the present invention provides a method of causing weight loss to treat obesity. The method includes introducing a gastric sponge device of the present invention into the stomach of a subject to cause satiety by occupying a volume of the stomach. In one embodiment, one or more sponge devices are introduced in a compressed configuration into the stomach via a delivery lumen advanced into the gastric cavity. In one embodiment, one or more sponge devices are introduced in a compressed configuration into the stomach via being loaded into a catheter and introduced through the accessory channel of an endoscope or alongside the scope and advanced into the stomach. Subsequently, the sponge expands upon hydration.

In various embodiments, the core region of the gastric sponge is composed of a biocompatible, sponge material that increases in volume upon absorption of fluid. The sponge material may be substantially non-degradable or be a material that degrades after a certain period of time, for example, after 1 day, 1 week, 1 month, 6 months or 1 year. In embodiments, the sponge may be composed of a variety of biocompatible materials so long as the materials are substantially non-degradable in an acid environment (for a desired period) and exhibit sponge like properties, for example the ability to expand and contract. Biocompatible, non-degradable sponge materials suitable for implantation include open cell foams, such as open cell polyurethane foams. Further, the foam material is ideally hydrophilic. In embodiments, the sponge device may be composed of foam material having a pore volume that is sized to only allow absorption of fluid. In various embodiments, the foam has a pore size of greater than or equal to about 100 ppi or 25 μm. For example, the pore size is between about 100 to 500 ppi, or about 100, 150, 200, 250, 300, 350, 400, 450 or 500 ppi. In similar embodiments, the pore size is between about 0.1 to 1000 μm, or about 0.1, 1, 5, 10, 25, 50, 100, 150, 200, 250, 500, 750 or 1000 μm. Further, in embodiments, the foam has a density of between about 0.01 to 0.2 g/cm$^3$, or about 0.6 to 1.0 g/cm$^3$. In one embodiment, the foam has a density of about 0.8 cm$^3$.

In various embodiments, the sponge material is capable of expanding in volume upon hydration. As is known in the art, the increase in volume will be dependent upon the properties of the material used, but typically it is capable of increasing in volume of greater than 5, 10, 15, 20, 30, 40, 50, 75, or even 100% from its compressed configuration upon complete saturation with a fluid. In some embodiments, the foam enables the core region to increase in volume about 10, 15, 20, 25 or 30% upon deployment and contact with a fluid as compared to a dry state. Additionally, in various embodiments, the core region is capable of a weight increase of at least about 5, 10, 15 or 20 times upon deployment and contact with a fluid as compared to a dry state.

In various embodiments, the gastric device may be composed of multiple materials, for example, foams having different properties. For example, a device may include a first region of foam having a first pore size or density, and a second region of foam having a second pore size or density which is different than the first. In this manner, the device may include 1, or more than 2, 3, 4, 5, 6, 7, 8, 9 or 10 foams. In embodiments, the device includes 1, 2, 3, 4, 5, 6, 7, 8, 9, 10 or more regions having different densities or pore sizes. In one embodiment, the device has a lower foam density at its surface and a higher foam density at its core. In another embodiment, the device has a higher foam density at its surface and a lower foam density at its core. In embodiments, the higher foam density may be a factor of 1, 5, 10, 50, 100, 1000 or more dense than the lower foam density. In one embodiment, the device has a foam having a smaller pore size at its surface and a larger pore size at its core. In one embodiment, the device has a foam having a larger pore size at its surface and a smaller pore size at its core. In embodiments, the larger pore size may be a factor of 1, 5, 10, 50, 100, 1000 or more greater than smaller pore size. Also, the foam material may be combined with non-foam materials, for example, materials that are not swellable, such as biocompatible polymers and the like.

In various embodiments, the outer casing is composed of a biocompatible, substantially non-degradable material. The outer casing may be composed of a variety of biocompatible materials so long as the materials are substantially non-degradable in an acid environment, such as silicon. In embodiments, the outer casing is composed of at least one material selected from the group consisting of polyethylene (PE), nylon, polyamide, polyether block amides (PEBAX), polyethylene terephthalate (PET), silicone, POC, polypropylene and polyether block PBT.

In various embodiments, the core surface may be coated with a lubricious coating. In some embodiments, the sponge has an exterior lubricious coating, such as a hydrophilic or silicone coating.

In various embodiments, the device may not include an outer casing but rather only have a core region and optionally a coating. In such embodiments, the density and pore size may be sized such that food particles are not absorbed into the core region. This may also be accomplished by application of a coating. As such, in various embodiments, the gastric device may include regions that are treated to block the adsorption of fluid and/or food particles in specific regions of the device. Such non-adsorptive polymers include those that are widely used in medical devices as described in U.S. Pat. Nos. 5,169,720 and 5,039,458, which are incorporated herein by reference. Other suitable coatings include hydrophilic coatings that are employed on surgical devices that work by creating a water barrier as described in U.S. Pat. Nos. 6,238,799 and 6,866,936, which are incorporated herein by reference.

In some embodiments, the device may include suture lines or stitching to connect the outer casing together and/or to the core region. Additional suitable materials useful for such applications include, but are not limited to, silicones, polytetrafluoroethylene (PTFE), polyether ether ketone (PEEK), and polypropylene. In one embodiment, the sponge device may include sutures of PEEK.

In various embodiments, the sponge device may further include a feature to allow for the device to be easily removed from the gastric cavity. In various embodiments, a device of the invention may include any number of such features, for example, at least 1, 2, 3, 4, 5, 6, 7, 8 or more such features. In some embodiments, the device includes multiple retrieval features located on opposing sides of the sponge. In some embodiments, the feature may be a fastener, hook/loop fastener (Velcro®), clip, button, magnet, keyhole or the like.

Figure 4:
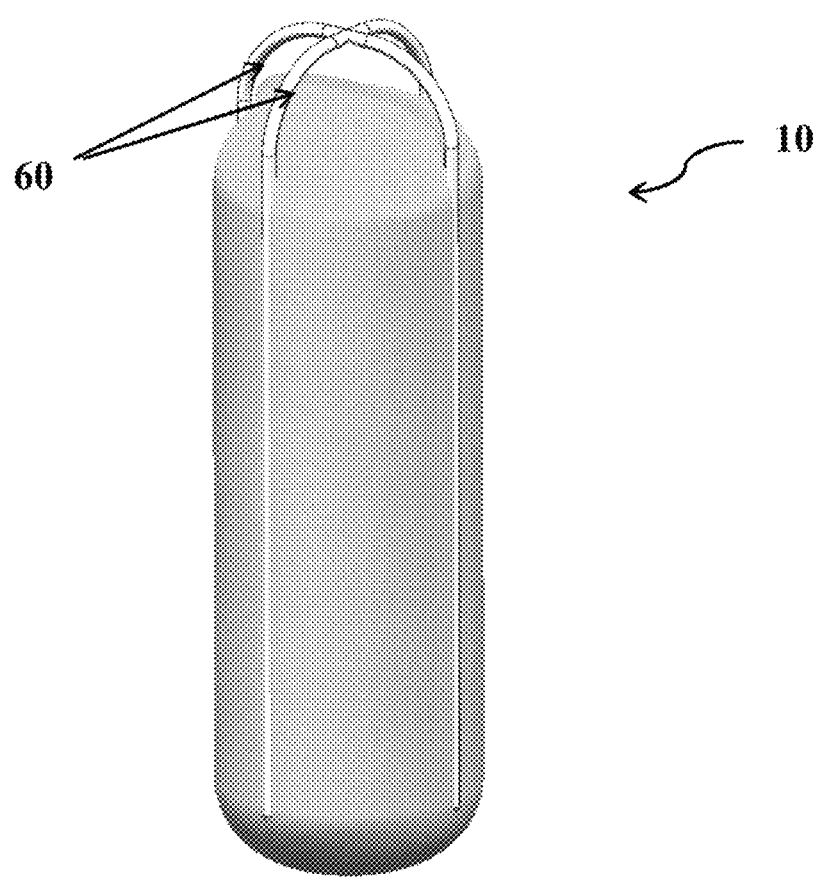
FIG. 4 is a schematic view of a sponge device in one embodiment of the invention in an expanded state.

FIG. 3 illustrates a device having a retrieval feature configured as a retrieval loop 60. The retrieval loop structure extends along the length of the body of the sponge to facilitate transmission and distribution of the pull force required to retrieve the device and pull the device into the lumen of an endoscope or overtube for example. Advantageously, the retrieval loop facilitates collapse of the sponge as it is drawn in a retrieval lumen as well as preventing contact of any seam in the casing that may be present at the loop end of the device with the stomach lining. FIG. 4 depicts a device having 2 retrieval loops 60. It is envisioned that the device may include up to 3, 4, 5, 6, 7, 8, 9, 10 or more retrieval loops. In one embodiment, one or more retrieval loops are disposed at each end of the device.

A retrieval loop of the invention may be composed of a resiliently flexible material that allows transition of the sponge between compressed and expanded states. By way of illustration, and in no way limiting, the retrieval loop may be composed of a resiliently flexible polymer or metal, such as nitinol.

FIG. 5A illustrates a sponge device which includes a tether 70 to facilitate retrieval of the device. It is envisioned that the device may include up to 3, 4, 5, 6, 7, 8, 9, 10 or more tethers.

Figure 6A:
FIG. 6A is a schematic view of a sponge device in one embodiment of the invention in an expanded state.
Figure 6B:
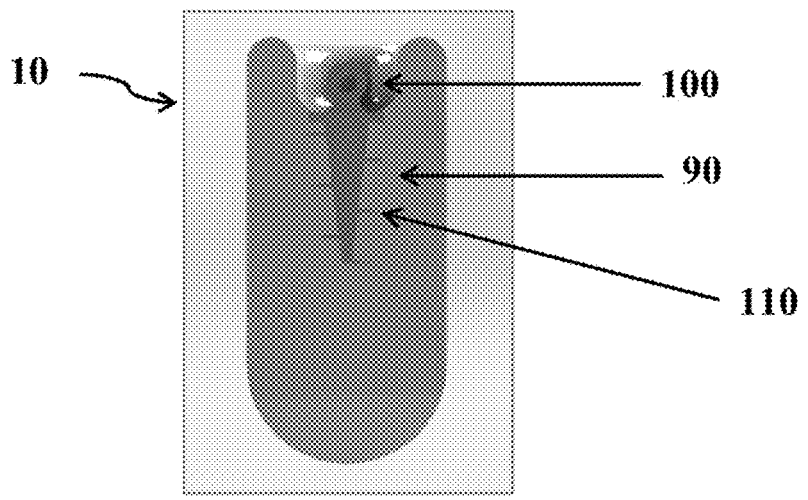
FIG. 6B is a cross-sectional view of the sponge device of FIG. 6B.
Figure 7:
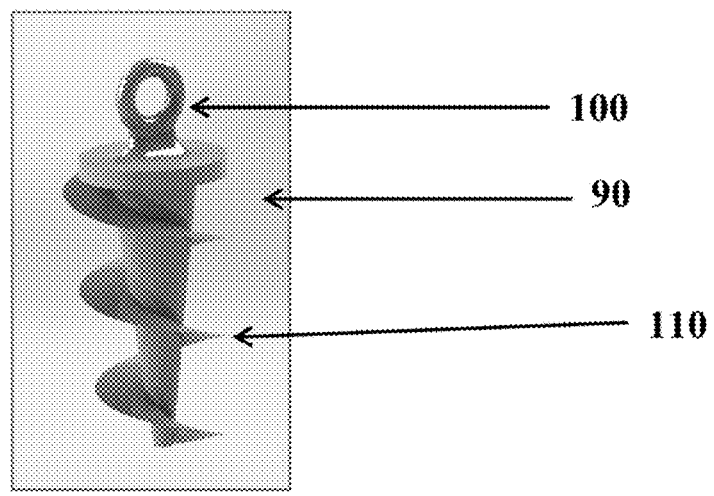
FIG. 7 is a schematic view of a retrieval feature for use with a sponge device in one embodiment of the invention.

FIGS. 6-7 illustrate a sponge device which includes a retrieval feature in one embodiment of the invention. The retrieval feature is essentially an screw anchor 90 having an eyelet 100. The screw is anchored into the sponge material via threads 110.

Figure 8A:
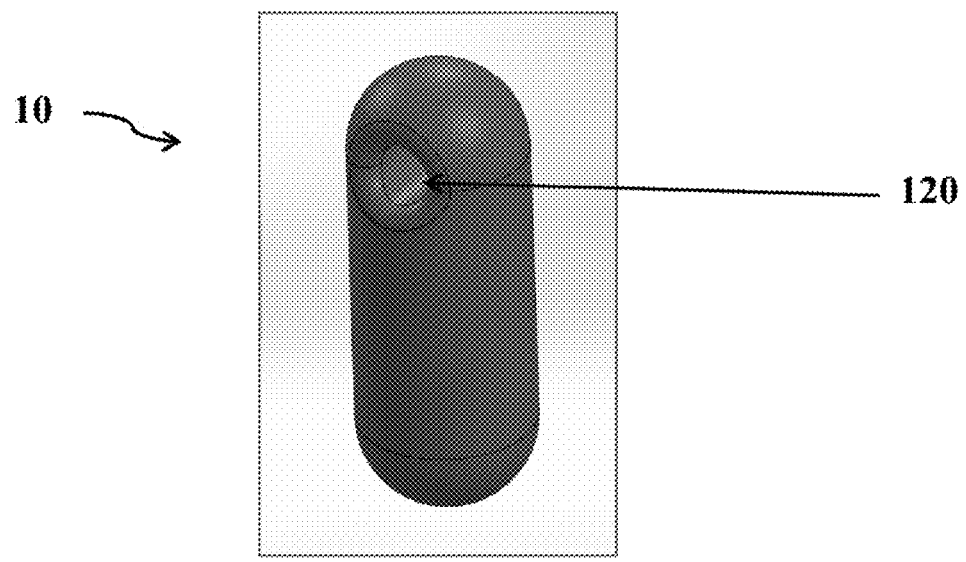
FIG. 8A is a schematic view of a sponge device in one embodiment of the invention in an expanded state.
Figure 8B:
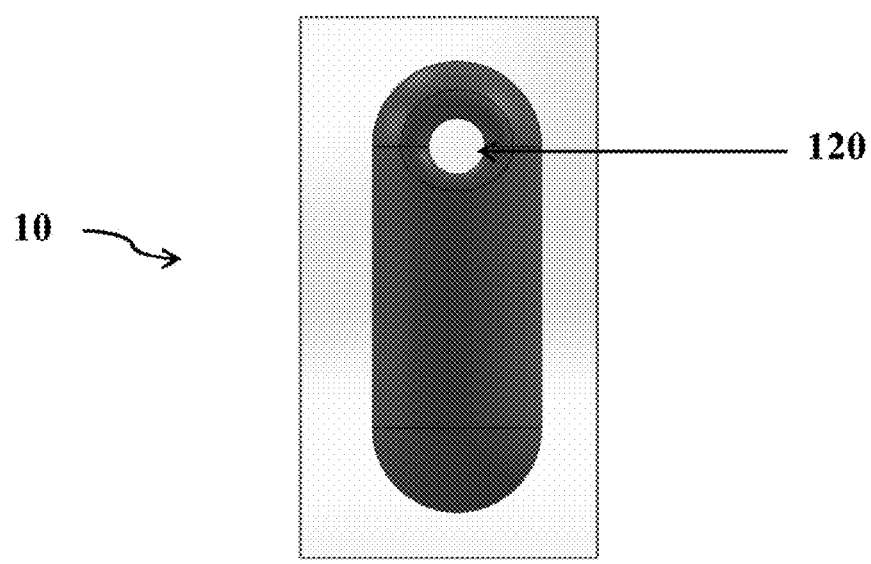
FIG. 8B is a side view of the sponge device of FIG. 8A.

FIGS. 8A-8B illustrate a sponge device having a retrieval feature in one embodiment of the invention. The retrieval feature is an eyelet 120 molded into the sponge defining a hole through the sponge such that a retrieval device can couple to the sponge. The eyelet 120 is easily coupled with a hook type retrieval device. In various embodiments, the eyelet is sized such that the hole is large enough to avoid particles of food from being trapped within the hole.

Figure 9A:
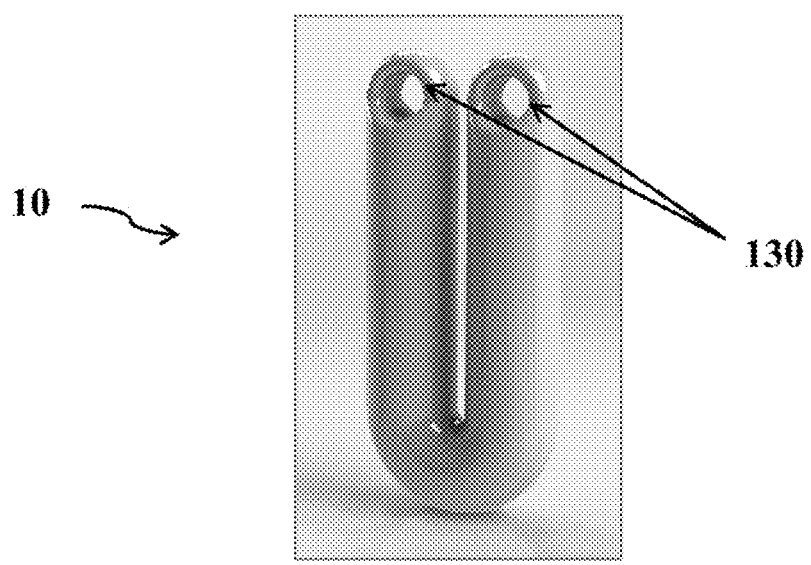
FIG. 9A is a schematic view of a sponge device in one embodiment of the invention in an expanded state.
Figure 9B:
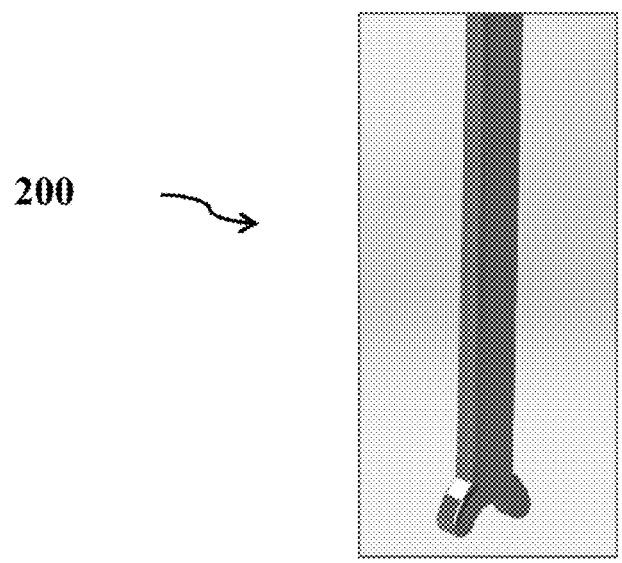
FIG. 9B is a schematic view of a pusher device which may be utilized to deploy the sponge device of FIG. 9A through a delivery lumen to the gastric cavity.
Figure 9C:
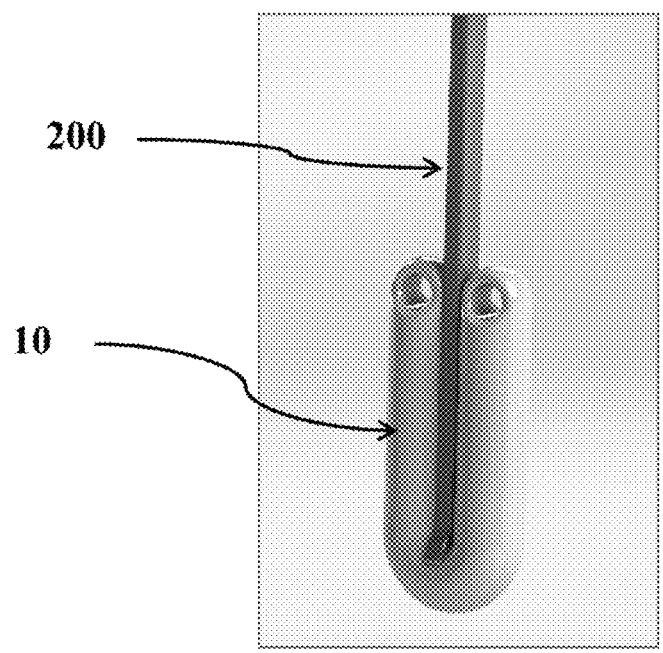
FIG. 9C is a schematic view of the pusher device of FIG. 9B engaging the sponge device of FIG. 9A during deployment of the device.
Figure 9D:
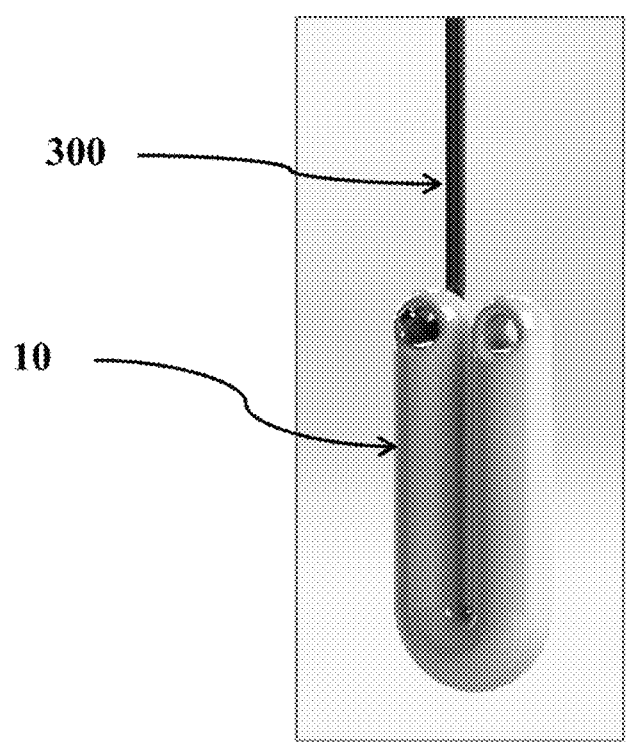
FIG. 9D is a schematic view of the sponge device of FIG. 9A engaged with a hook type retrieval device.
Figure 9E:
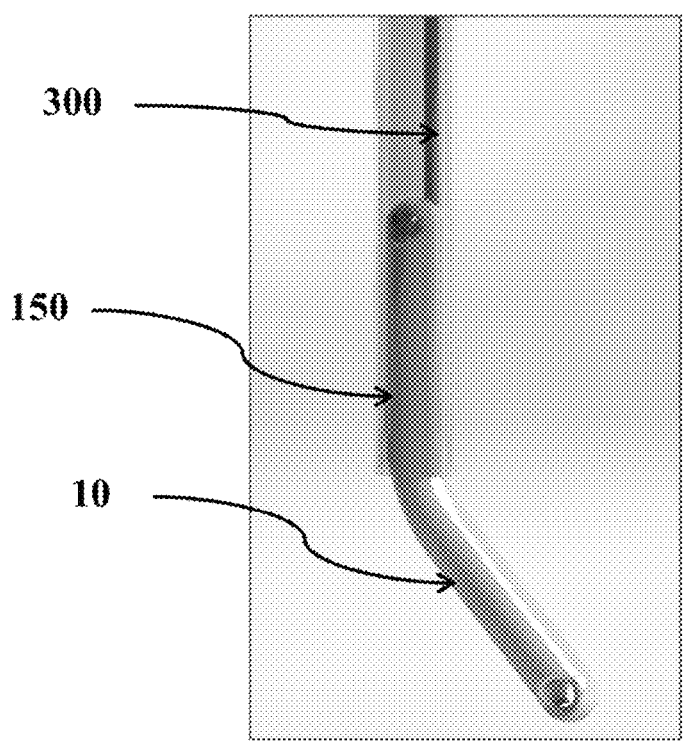
FIG. 9E is a schematic view of the sponge device of FIG. 9A engaged with the hook type retrieval device of FIG. 9D during withdrawal of the device.

FIGS. 9A-9E illustrate a system of the invention having a sponge device including multiple retrieval features. FIG. 9A depicts a sponge device 10 which includes eyelets 130 molded into the sponge defining holes through the sponge such that a retrieval device can couple to the sponge. The eyelets are disposed on opposing distal and proximal ends of the cylindrical shaped sponge. The device is shown in a folded configuration in FIG. 9A which is the configuration of the device upon being loaded in a delivery lumen for deployment in the gastric cavity. The device is advanced out of the delivery lumen via pusher apparatus 200 shown in FIGS. 9B-9C. To retrieve the device from the gastric cavity, a hook type retrieval tool is utilized to engage eyelet 130 as shown in FIGS. 9D-9E. With reference to FIG. 9E, the device 10 is retrieved via retrieval tool 300 which is used to pull the sponge into the lumen of a retrieval device 150 wherein the sponge is not folded as in delivery. This allows a small diameter device to be used for retrieval as compared to delivery.

Figure 10A:
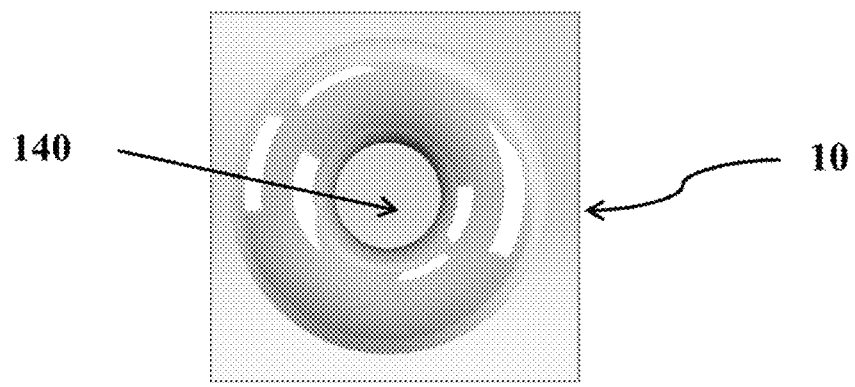
FIG. 10A is a top view of a sponge device in one embodiment of the invention in an expanded state.
Figure 10B:
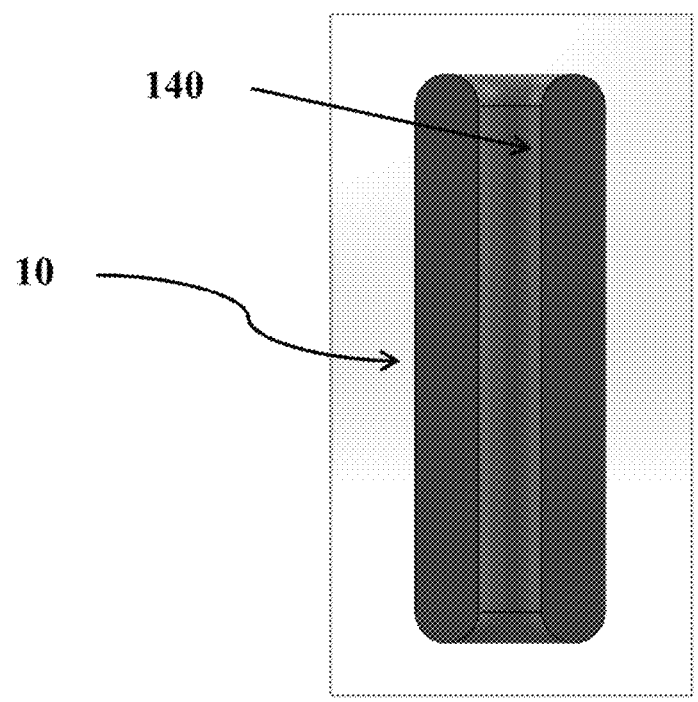
FIG. 10B is a cross-sectional side view of the sponge device of FIG. 11A.

In various embodiments, the sponge device of the invention may include features that facilitate compression of the sponge such the less force is required to compress the sponge and/or to reduce the volume of the device when in the compressed state. As such, the sponge device may include one or more hollow lumens or voids within the core region. FIGS. 10A-10B illustrate a sponge device having a single lumen 140 disposed along the elongated central axis of the device. It will be appreciated that the sponge device may include multiple lumens, for example, 2, 3, 4, 5, 6, 7, 8, 9, 10 or lumens to reduce volume in the compressed state. It will also be appreciated that the lumens may be of any desired shape or size. In embodiments, the lumen is a tubular or spherical void having a diameter less than the outer diameter of the gastric device, for example, about 0.1 to 6.0 inches, 0.5 to 6.0 inches, 0.1 to 5.0 inches, 0.1 to 4.0 inches, 0.1 to 3.0 inches, 0.1 to 2.0 inches, 0.1 to 1.0 inches, 0.1 to 0.9 inches, 0.1 to 0.8 inches, 0.1 to 0.7 inches, 0.1 to 0.6 inches, 0.1 to 0.5 inches, 0.1 to 0.4 inches, 0.1 to 0.3 inches, or 0.1 to 0.2 inches. In various embodiments, the cross-sectional shape of the lumen may be any geometric shape, such as, for example, circular, elliptical, square, triangular, rectangular, star shaped, polygon shaped, and the like.

The sponge device generally depicted throughout FIGS. 1-10 is generally cylindrical or tubular in shape. However it will be appreciated that the sponge device may have various geometries. The sponge device may be of any shape, since the sponge material is compressible to facilitate implantation. For example, by way of illustration, the sponge shape may be cylindrical, spherical, ellipsoid, toroidal, tubular, or any other geometry generally known in the art. In exemplary embodiments (e.g., as shown in FIGS. 1-10), the sponge may have a compressed configuration that is generally cylindrical or capsule-shaped before deployment in the stomach. Upon delivery into the stomach, the device generally maintains its original shape as it expands thereby preventing migration of the device distally through the pylorus and to ensure that the device remains in the stomach until it is retrieved.

Figure 11:
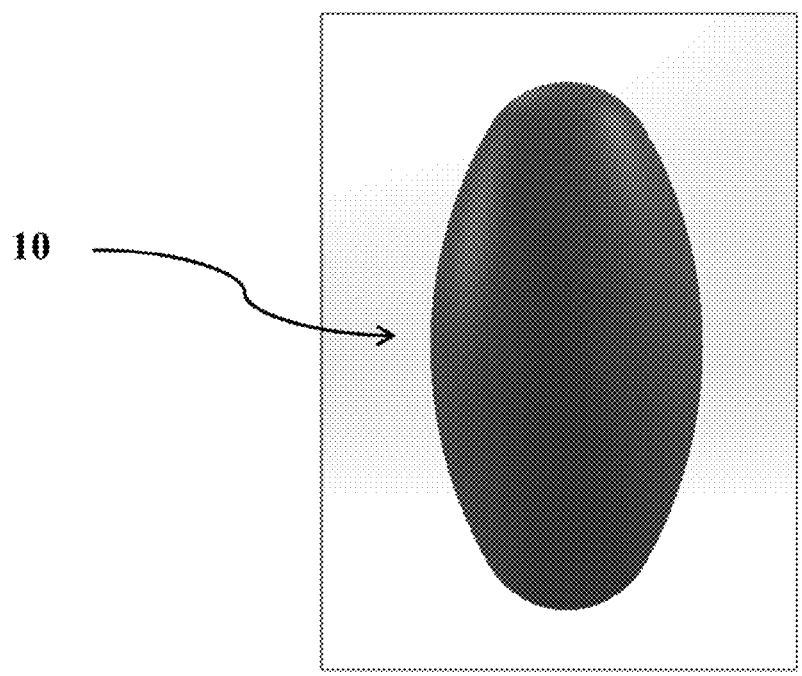
FIG. 11 is a schematic view of a sponge device in one embodiment of the invention in an expanded state.
Figure 12:
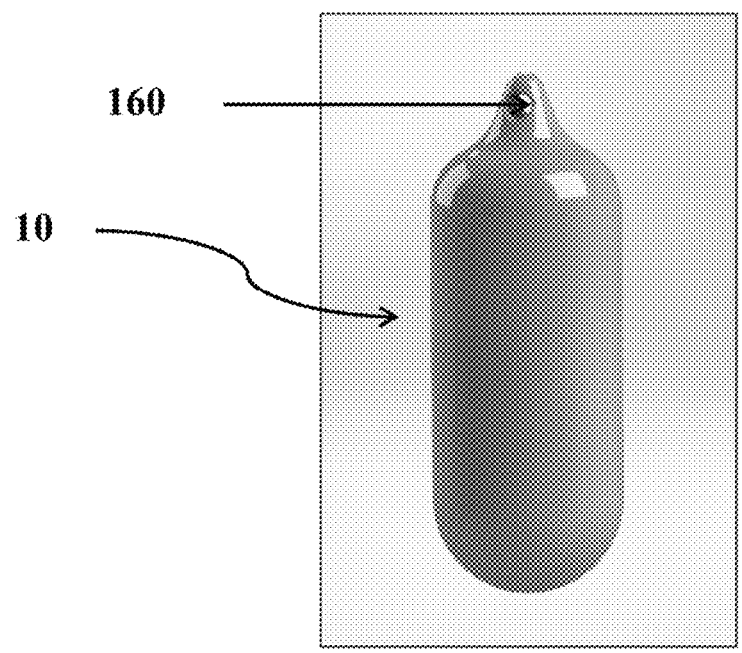
FIG. 12 is a schematic view of a sponge device in one embodiment of the invention in an expanded state.

FIG. 11 shows a sponge device 10 which generally has an ellipsoid geometry when expanded. In this configuration, the central region of the sponge has a greater diameter than the tip regions. In this configuration, when the sponge is in the collapsed or compressed state within a lumen, the maximum radial force is at the equator of the sponge. As such, less force at the proximal and distal ends facilitate delivery and retraction of the device. This can also be achieved by providing a taper to the proximal end and/or distal end as shown in FIG. 12 which illustrates a sponge geometry having a taper integral with the retrieval feature 160.

Figure 13A:
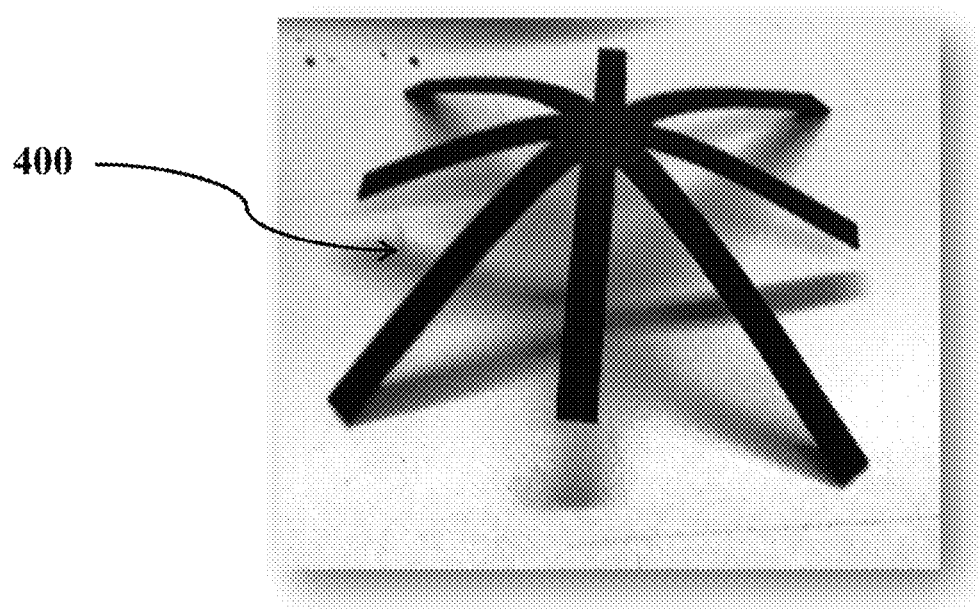
FIG. 13A is a schematic view of a resiliently deformable structure which is coupled to a sponge and operable to assist in collapsing the sponge upon retrieval in one embodiment of the invention.
Figure 13B:
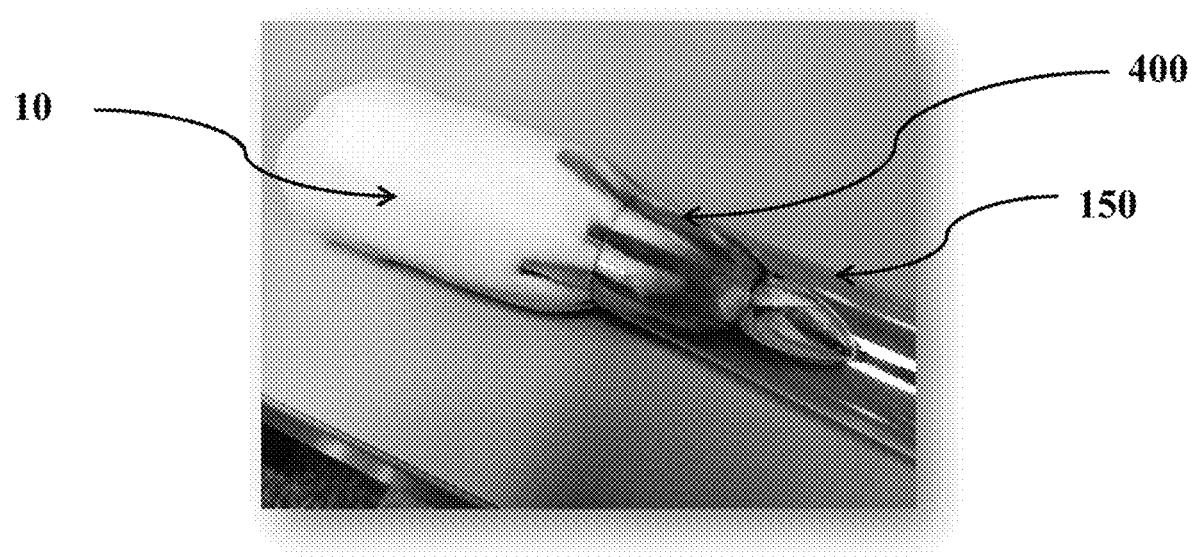
FIG. 13B is a schematic view of the resiliently deformable structure of FIG. 13A coupled to a sponge device.

As discussed herein, the sponge device of the present invention may include additional features that facilitate retraction of the device by allowing the sponge to be compressed within the lumen of a retrieval device upon withdrawal from the gastric cavity. In the embodiment depicted in FIGS. 13A-13B, the sponge 10 further includes a resiliently deformable structure 400 coupled to the sponge which is operable to assist in collapsing the sponge into a lumen 150 upon retrieval. The structure may include a plurality of arms (e.g., 2, 3, 4, 5, 6 7, 8, 9, 10 or more) which generally form an umbrella structure having a central point which is aligned with the retrieval feature of the sponge such that the structure enters the lumen with the retrieval feature upon retrieval of the device.

Figure 14:
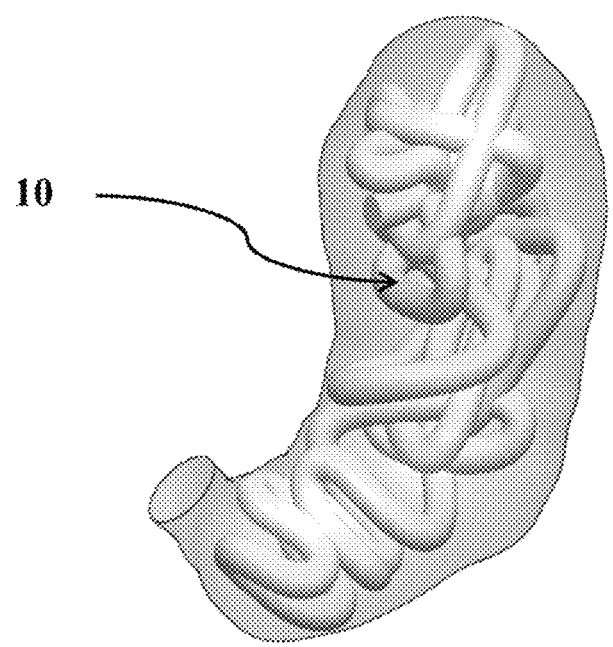
FIG. 14 is a schematic view of a sponge device in one embodiment of the invention in an expanded state deployed within a gastric cavity.
Figure 15:
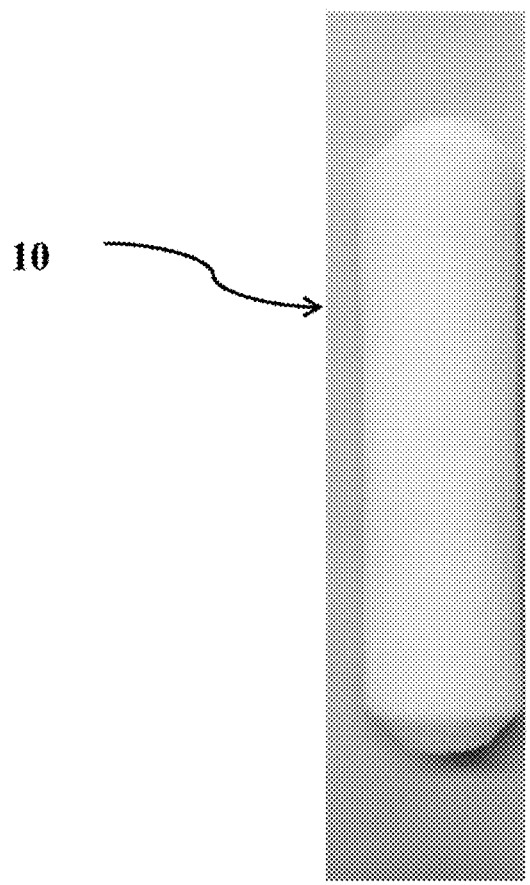
FIG. 15 is a schematic view of a sponge device in one embodiment of the invention. The device has distal and proximal tapered ends and is 4 inches in length and has an outer diameter of 1 inch.
Figure 16:
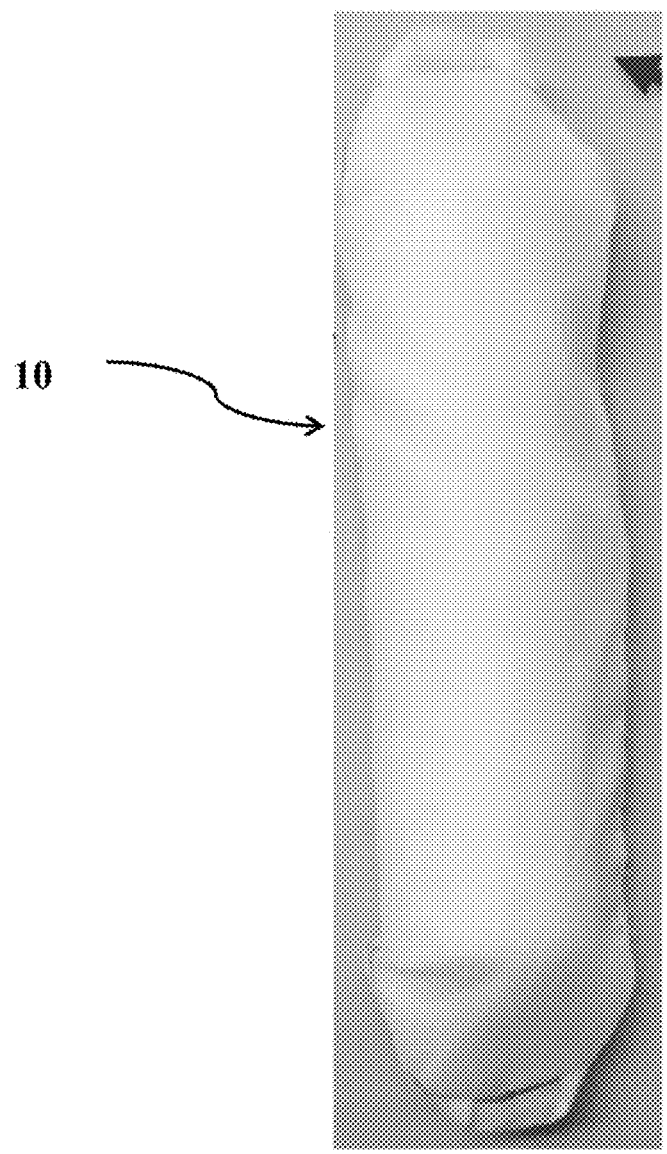
FIG. 16 is a schematic view of a sponge device in one embodiment of the invention. The core is the device shown in FIG. 15 with an outer casing having deformable capture loops. Upon hydration, the core fills out that outer casing.
Figure 17:
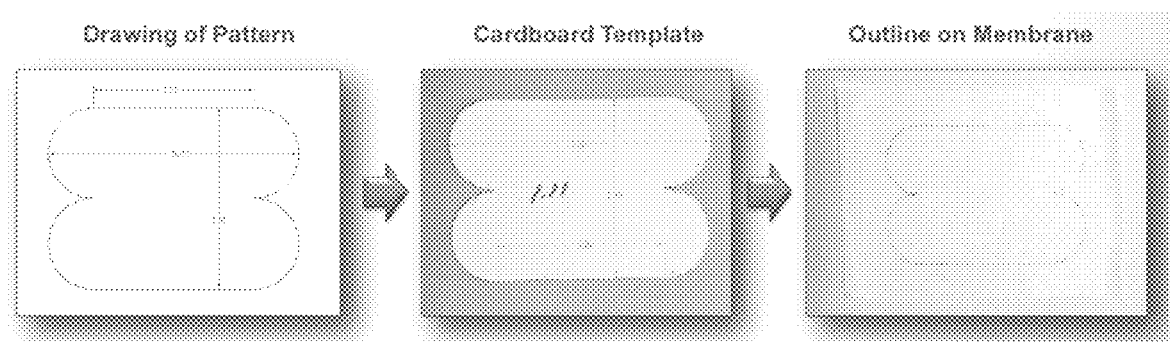
FIG. 17 is a flow diagram showing the manufacture process of the outer casing of the device of FIG. 16. Once cut, the casing is sewn around the core.

FIG. 14 depicts an embodiment of the invention, in which the gastric device is configured as a cylinder or tube having an elongated length. In this embodiment, the volume of the stomach may be determined prior to deployment. The device length is varied depending on how much gastric volume is desired to be occupied. In this embodiment, the gastric device may be formed of a sponge material or be composed of a non-expanding material. The device may include one or more lumens traversing the elongated length of the sponge. Further, the device may include a shape memory element, such as a shape memory alloy (e.g., nitinol), which allows the device to assume a predetermined shape upon deployment. One or more gastric devices may be utilized following this methodology.

In various embodiments, the sponge device may also include regions that are radiopaque to facilitate imaging of the device. The device may be entirely radiopaque or on only portions may be radiopaque, such as the cylindrical tips.

As discussed herein, the device may be pre-sized to occupy a particular volume of the stomach upon being fully expanded. Additionally, multiple devices may be implanted in unison to achieve the desired result. In various embodiments, the device has a cylindrical diameter of about 1.0 to 2.0 inches and a length of about 1.0 to 6.0 inches, a cylindrical diameter of about 1.0 to 1.75 inches and a length of about 3.0 to 6.0 inches, or a cylindrical diameter of about 1.25 to 1.5 inches and a length of about 4.0 to 6.0 inches. In one embodiment, the device has a cylindrical diameter of about 1.25 inches and a length of about 3.5, 3.75, 4.0, 4.25, 4.5, 4.75, 5.0, 5.25, 5.5, 5.75 or 6.0 inches and is capable of being delivered through a tube having an inner diameter of about 12, 13, 14, 15, 16 or 17 mm. Depending on the size of the device and the size of the gastric space, up to 1, 2, 5, 7, 10, 15, 20, 25, 30 or more individual devices may be implanted. In one embodiment, the gastric device has a pore size of about 25 μm, with a length of about 4 inches and a diameter of about 1 inch in a dried uncompressed state; and in a fully hydrated state the device has a length of about 4.6 inches and a diameter of about 1.2 inches.

In various embodiments, the core region may be manufactured by cutting the device from a sheet of foam stock, and optionally, subsequently tapering the ends if desired.

Accordingly, in embodiments, the system of the invention may include multiple gastric sponge devices, which may be reversibly coupled together. Coupling may be done prior to delivery, or at any time after the sponge devices are deployed in the gastric cavity.

To determine the appropriate size of the device(s) for an individual subject, the size of the subject's stomach is measured before implantation of the device. A variety of techniques may be employed to determine the volume of the stomach. For example, x-ray or other types of imaging may be used. In an exemplary embodiment, the stomach volume is determined using a gastric sizing balloon catheter. The catheter includes a balloon at its distal tip. The catheter is advanced into the stomach and the gastric balloon inflated with a fluid, such as water, air, radiopaque material, or the like until it occupies the desired volume of the stomach, e.g., 40, 50, 60, 70, 80 or 90% of the total volume of the gastric lumen. The sizing procedure may be performed under endoscopic and/or radiologic guidance. The volume of fluid inserted that results in the desired occupancy of the stomach by the balloon is used to determine the size of the gastric sponge.

The gastric sponge may be deployed within the stomach for various durations before being retrieved. In various embodiments, the device is deployed in the stomach for about 1-7 days, 1-2 weeks, 2-4 weeks, or several months. Upon retrieval, the sponge may be disposed of and a new gastric sponge (potentially of larger or smaller size than the retrieved sponge) deployed, the process continuing until the desired weight of the subject is achieved.

As used herein, the term "subject" is intended to refer to any individual or patient to which the method described herein is performed. Generally the subject is human, although as will be appreciated by those in the art, the subject may be an animal. Thus other animals, including mammals such as cats, dogs, farm animals including cows, horses, goats, sheep, pigs, and the like, as well as primates (including monkeys, chimpanzees, orangutans and gorillas) are included within the definition of subject.

In yet another aspect, the present invention provides a device operable to couple or grasp an object, such as a medical implant or the gastric device of the disclosure. While the device is discussed with reference to retrieving a gastric implant, it will be appreciated that the device may be used to grasp or couple with any type of medical device or object. As such, the disclosure also provides a method of grasping or coupling an object using the device of the disclosure.

With reference to FIGS. 21-25, the device 700 includes an elongated shaft 730 extending from a proximal end to a distal end along a longitudinal axis. The shaft 730 has a lumen extending along the longitudinal axis, wherein the distal end comprises a coupling structure 710 operable to couple to, or grasp an object, such as a gastric device. A handle 720 or grip is disposed proximally on the shaft 730 suitable for grasping by a physician's hand.

Figure 21:
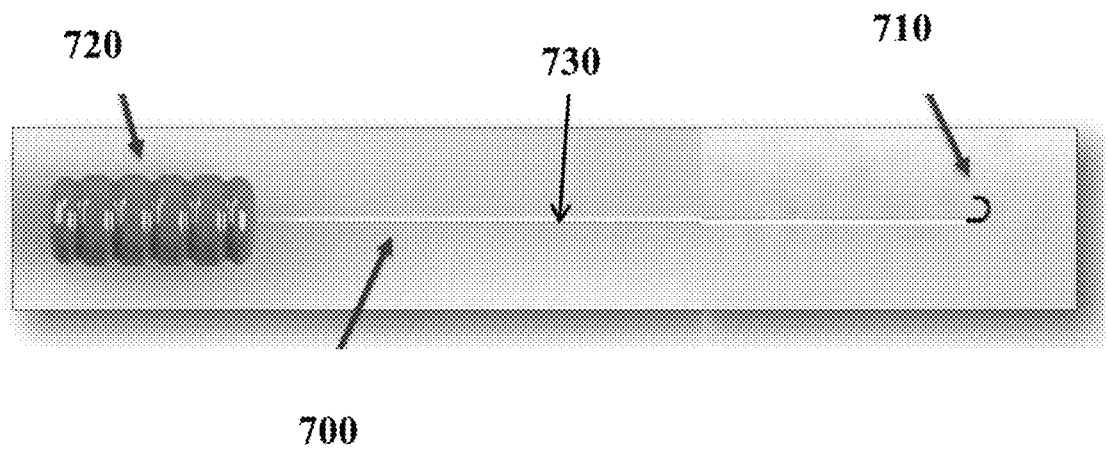
FIG. 21 is a schematic view of a retrieval device 700 suitable for retrieval of an implant.

FIG. 21 is a schematic view of a retrieval device 700 suitable for retrieval of an implant. The retrieval device includes a distally disposed coupling structure 710 and a proximally disposed handle 720 which is removable so that the device may be loaded through a gastroscope. The coupling structure is hook shaped and is rounded such that it is atraumatic. Further, the shaft 730 is semi-flexible and torqueable.

Figure 22:
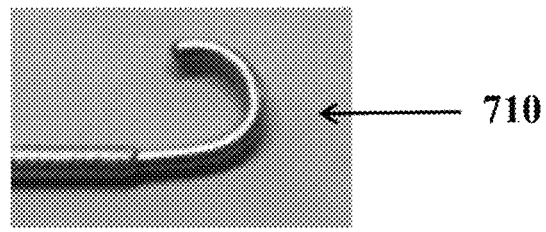
FIG. 22 is an expanded view of a coupling structure 710 in one embodiment of the invention.
Figure 23:
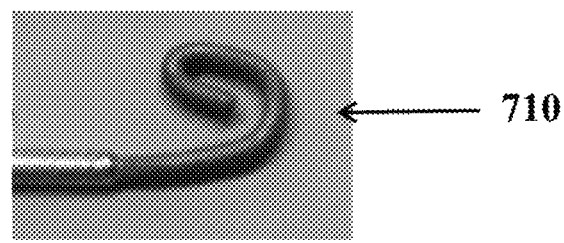
FIG. 23 is an expanded view of a coupling structure 710 in one embodiment of the invention.

FIGS. 22 and 23 show coupling structures 710 having a hook or circular shape.

Figure 24A:
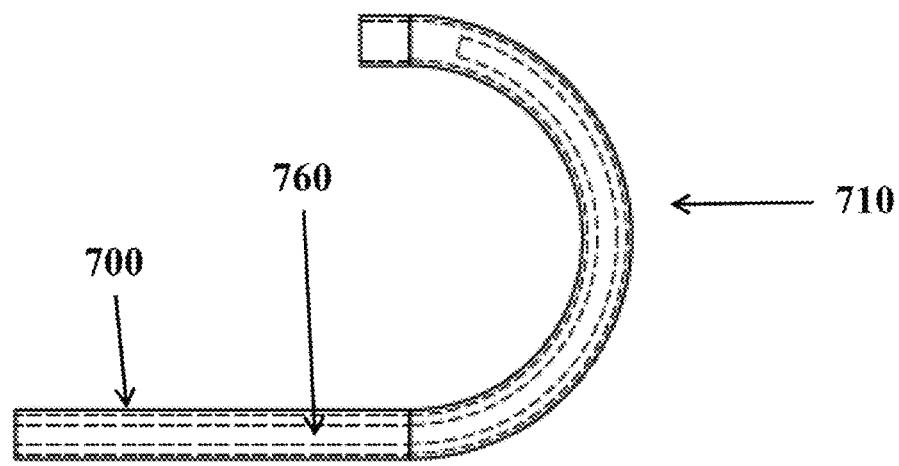
FIG. 24A is an expanded view of a coupling structure 710 in one embodiment of the invention.

FIG. 24A is an expanded view of a coupling structure 710 in one embodiment of the invention. The structure is shown in an open position such that an implant can be engaged. The shaft 700 is configured as a tube having an inner wire or rod 760. Both may be formed of a polymer, nitinol, stainless steel, or other strong metal or metal-alloy common to endoscopic tools. The rod 760 traverses the length of the shaft lumen to the proximal end of the device. The coupling structure 710 may be opened or closed by a physician via an actuator element disposed proximally on the device (not shown), such as in the handle. In this embodiment, the rod 760 is slidably disposed within the shaft lumen such that the couple structure is closed when the rod 760 is advanced distally relative to the shaft. In this embodiment, the shaft is formed from a material that is stronger/stiffer than the rod material so that the distal formed hook shape is able to withstand the high forces that may be associated with recovery/retrieval of a large object into a small recovery tube. The rod 760 may be formed from a more deflectable material as compared to the shaft so that its shape conforms to the shaft shape when the rod is actuated proximally into the tube, rather than overpowering and deforming the shape of the outer tube.

Figure 24B:
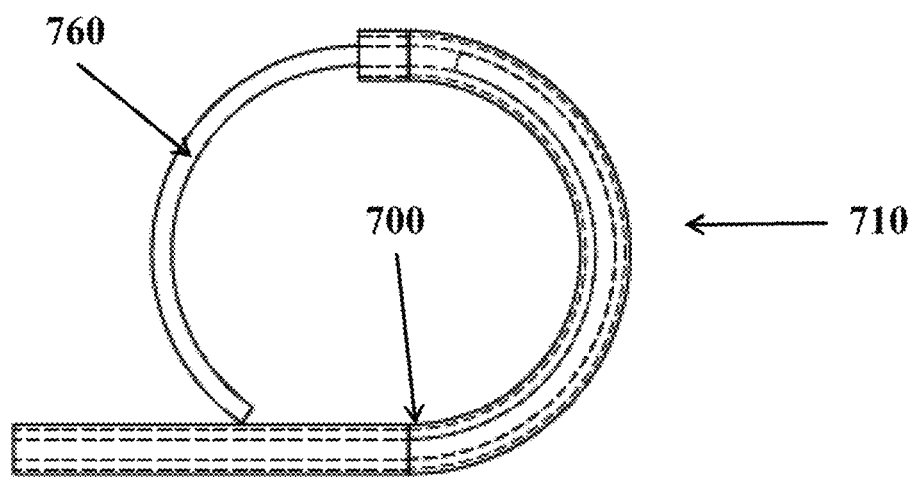
FIG. 24B is an expanded view of the coupling structure 710 of FIG. 24A. The structure is shown in a closed position.

FIG. 24B is an expanded view of the coupling structure 710 of FIG. 24A. The structure is shown in a closed position.

Figure 25:
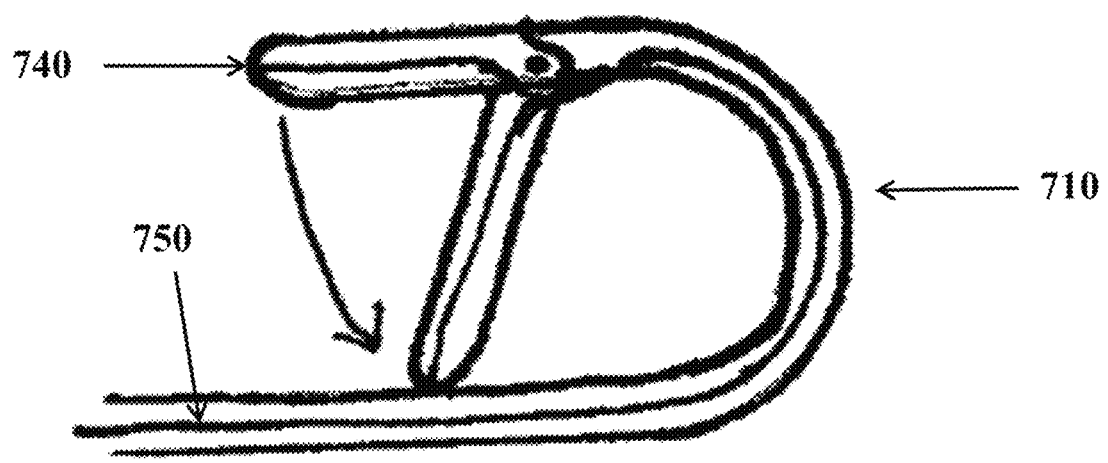
FIG. 25 is an expanded view of a coupling structure 710 in one embodiment of the invention.

FIG. 25 is an expanded view of a coupling structure 710 in one embodiment of the invention. Finger element 740 can be opened or closed by a physician via an actuator element disposed proximally on the device (not shown), such as in the handle. In this embodiment, the finger element 740 is mechanically coupled to the actuator element via a wire 750.

In various embodiments, the coupling structure may be hook shaped having a constant or variable radius of curvature. In embodiments, the radius is greater than or equal to about 0.25, 0.5, 0.75, 1, 1.25, 1.5, 1.75, 2, 2.25, 2.5, 2.75, 3, 3.25, 3.5, 3.75, 4, 4.25, 4.5, 4.75 or 5 cm.

It will be understood that the coupling structure may be operable in a variety of ways to retrieve an object depending on the type of retrieval element present on the object. For example, the coupling structure may include a fastener, hook/loop fastener (Velcro®), clip, button, magnet, key, keyhole or the like.

In embodiments, the system of the invention is utilized to deliver and retrieve a gastric device to and from the stomach of a patient. First, a delivery device having a delivery lumen (with pre-loaded implant) is inserted through an overtube. A pusher device (FIG. 20) is introduced in to the delivery tube and advanced to the proximal marker. The pusher is slowly advanced to the distal marker indicating full deployment of the implant. The pusher device is then withdrawn along with the delivery tube. This process is repeated for each additional implant that is administered as necessary. For retrieval, the retrieval device of the invention (FIGS. 21-25) is utilized. The retrieval hook is backloaded into a gastroscope and a handle is attached to the proximal end. The gastroscope with the retrieval hook is then loaded into the capture tube (FIGS. 18-19) and the entire assembly inserted through an overtube. Using the gastroscope for navigation, the capture loop of an implant is hooked and the implant pulled back into the capture tube. The retrieval hook and scope are then pulled back together through the capture tube.

In various embodiments, the system of the invention may be operable to deliver or administer a substance directly to the stomach of the patient. In various embodiments, the substance may be a fluid or solid, including for example, nutritional supplements, vitamins, drugs, water, and the like. In such embodiments, the substance may be delivered in the same manner a gastric device is delivered, for example, through a delivery lumen optionally utilizing a pusher device. In embodiments, the substance may be delivered along with a gastric device. In some embodiments, the substance is included in the gastric device. As such, the invention further provides a method of delivering a substance to the stomach of a subject using a gastric device or system of the invention.

In various embodiments, a sponge device of the invention may be delivered to a bodily lumen other than a gastric cavity. As such, the invention provides a method of delivery an implant device of the invention to a bodily lumen or cavity of a subject. As used herein, a "bodily lumen" may include and enclosed space with a subject, such as, an organ, tissue, or the like that includes a partially or fully enclosed cavity. To facilitate delivery and retrieval, the system of the present invention may be utilized.

In embodiments, a gastric device may be encapsulated in a delivery capsule for delivery. The device may be compressed and encapsulated in a degradable shell and delivered with or without a delivery lumen. In one embodiment, the capsule is delivered without use of a delivery lumen. For example, the device may be encapsulated in a degradable capsule and ingested by the patient. Once in the stomach, the capsule lining degrades thereby allowing the device to expand within the stomach. The number of capsules ingested by the patient may be determined by a physician based on the patient's gastric volume. The methodology avoids an endoscopic delivery procedure and allows the capsules to be taken over time in necessary.

The skilled person will appreciate that the capsule may be of any size provided that the external capsule is of a size that can be swallowed easily. In embodiments, the capsule may have an overall length of about 5, 10, 15, 20, 25 or 50 mm and an external diameter of less than about 15, 12, 10, 9, 8, 7, 6, 5 or 4 mm.

Capsules for human use come in standard sizes that conform to a numbering system, which indicates their length, diameter and volume. The largest capsule employed for human ingestion is referred to as a size #000, whereas the smallest is a size #5. A size #000 capsule will typically have a diameter of about 9.9 mm and a locked length of about 26.1 mm. Any size capsule may be used with the present invention, for example #000, #00E, #00, #0E, #0, #1, #2, #3, #4, or #5.

Capsules are available in a wide variety of types and any capsule is contemplated for use in the present invention so long as the capsule is dissolvable. Capsules include hard gelatin capsules, soft elastic capsules, or hydroxypropylmethylcellulose (HPMC) capsules. Examples of capsules include a gelatin capsule such as the CONI-SNAP™ capsule (trade name, commercially available from CAPSUGEL™ AG, a Pfizer company), a corn starch capsule such as CAPILL™ (trade name, commercially available from Warner-Lambert Company, U.S.A.), a hydroxypropylmethylcellulose capsule such as HPMC™ capsule (trade name, commercially available from Japan ELANCO, Japan) and the like.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The following examples are provided to further illustrate the embodiments of the present invention, but are not intended to limit the scope of the invention. While they are typical of those that might be used, other procedures, methodologies, or techniques known to those skilled in the art may alternatively be used.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Gastric Sponge System

A gastric sponge device of the present invention (as shown in FIGS. 5A-5B) was manufactured and tested. Briefly, the device included an open cell polyurethane foam inner core and silicone outer casing. The shape of the devices are shown in FIGS. 5A and 5B and had an outer diameter of 1.25 inches with a length of 3.75 inches.

20 sponges were implanted into the stomach of a live pig where they remained for 4 weeks. Weight loss was observed over the test period as follows. Final pig body weight= 88 lbs (←106 lbs at 2nd wk←101 lbs at 1st week after procedure←107 lbs before procedure).

At the end of the test period, the esophagus was determined to be normal upon examination. The stomach was determined to be filled with sponges and moderate amount of residual food. There was no mucosal erosions or ulcers in the stomach. The vast majority of the sponges remained intact and were prevented from migrating through the pyloric sphincter.

CONCLUSION

This study showed feasibility of the sponge system to be successful in inducing weight loss.

Although the invention has been described with reference to the above examples, it will be understood that modifications and variations are encompassed within the spirit and scope of the invention. Accordingly, the invention is limited only by the following claims.

What is claimed is:

1. A gastric sponge suitable for placement in a stomach of a subject, the sponge comprising:
   a) a core region composed of an open cell foam material that is substantially acid resistant and non-degradable in the stomach, and which expands in volume upon absorption of fluid;
   b) an outer casing disposed about the core region, the outer casing being composed of a material that is substantially acid resistant and non-degradable in the stomach; and
   c) a retrieval loop coupled to the sponge,
   wherein the sponge has a compressed configuration and an uncompressed deployed configuration, both configurations having a generally cylindrical shape, and
   wherein the sponge has a length which extends along an elongated central axis, the sponge having a proximal end and a distal end arranged along the central axis, and
   wherein portions of the retrieval loop that extend along the length of the sponge, extend parallel to and along the elongated central axis from the proximal end toward the distal end on opposing sides of the sponge, and
   wherein a portion of the retrieval loop extends beyond the proximal end of the sponge, and
   wherein the retrieval loop is operable to facilitate transmission and distribution of force required to compress and retrieve the sponge from the stomach.

2. The sponge of claim 1, wherein the open cell foam material is hydrophilic.

3. The sponge of claim 2, wherein the open cell foam material is a polyurethane foam.

4. The sponge of claim 3, wherein the foam has a pore size of greater than about 100 ppi.

5. The sponge of claim 3, wherein a pore size of the foam is between about 100 to 500 ppi.

6. The sponge of claim 3, wherein the core region is capable of a volume increase of up to about 10, 15, 20, 25 or 30% upon deployment and contact with a fluid as compared to a dry state.

7. The sponge of claim 3, wherein the core region is capable of a weight increase of at least about 5, 10, 15 or 20 times upon deployment and contact with a fluid as compared to a dry state.

8. The sponge of claim 3, wherein the foam has a density of about 0.01 to 0.2 g/cm3.

9. The sponge of claim 3, wherein the foam has a density of about 0.6 to 1.0 g/cm3.

10. The sponge of claim 1, wherein the outer casing comprises one or more openings operable to allow fluid flow across the casing to and from the core region.

11. The sponge of claim 10, wherein the one or more openings are sized to only allow absorption of fluids.

12. The sponge of claim 11, wherein the one or more openings are configured as slits extending along the length of the sponge.

13. The sponge of claim 12, wherein the slits are arranged radially about the central axis.

14. The sponge of claim 1, wherein the outer casing comprises a plurality of pores.

15. The sponge of claim 14, wherein the pores have a pore size of between about 1-100 μm.

16. The sponge of claim 15, wherein the pore size is about 25 μm.

17. The sponge of claim 1, wherein the outer casing is composed of at least one material selected from the group consisting of polyethylene (PE), nylon, polyamide, polyether block amides (PEBAX), polyethylene terephthalate (PET), silicone, POC, polypropylene and polyether block PBT.

18. The sponge of claim 1, wherein the sponge has an exterior lubricious coating selected from the group consisting of hydrophilic coatings and silicone coating.

19. The sponge of claim 1, wherein the sponge is shaped to prevent migration of the device through the pyloric valve.

20. The sponge of claim 1, wherein the length of the sponge is about 1 to 6 inches and a diameter of the sponge is about 1 to 2 inches in the deployed configuration.

21. The sponge of claim 20, wherein the length of the sponge is about 1 to 6 inches and a diameter of the sponge is about 1 to 1.5 inches.

22. The sponge of claim 20, wherein the core region comprises at least one hollow lumen extending along the central axis.

23. The sponge of claim 1, wherein the core region comprises at least one hollow lumen.

24. The sponge of claim 1, wherein the sponge further comprises a resiliently deformable structure coupled to the sponge, the structure operable to assist in collapsing the sponge into an overtube upon retrieval.

25. The sponge of claim 1, wherein the sponge further comprises a shape memory material configured to define a desired shape upon deployment of the sponge.

26. The sponge of claim 1, wherein the sponge comprises a radiopaque material.

27. The sponge of claim 1, wherein the sponge is adapted for placement in the stomach without substantial degradation for a duration of any period between one day and several months or years, or with degradation sufficient to allow migration through the GI tract after a duration of any period between one day and several months or years.

28. The sponge of claim 1, wherein the core region and the outer casing are connected via one or more sutures.

29. The sponge of claim 28, wherein the one or more sutures is composed of polyether ether ketone (PEEK).

30. The sponge of claim 1, further comprising a substance selected from a drug, vitamin, nutritional supplement, fluid, food stuff, therapeutic or pharmaceutical agent, and combination thereof.

31. A system comprising the sponge of claim 1, wherein the system further comprises a delivery device having a lumen for delivery or retrieval of the sponge from the stomach.

32. The system of claim 31, further comprising a retrieval device for attachment to the sponge, wherein the retrieval device is deployed through the delivery device lumen and operable to couple to the sponge in the stomach and retract the sponge into the lumen, wherein retracting the sponge into the lumen causes the sponge to substantially return to its compressed configuration.

33. The system of claim 32, further comprising a catheter.

34. The system of claim 31, comprising at least two sponges coupled together.

* * * * *